United States Patent [19]
Mann et al.

[11] 4,245,641
[45] Jan. 20, 1981

[54] DISPLAY AND CONTROL SYSTEM AND METHOD FOR PROGRAMMABLE LIVING TISSUE STIMULATOR

[75] Inventors: Brian M. Mann, Northridge; Jason A. Sholder; Marc I. Hurowitz, both of Canoga Park, all of Calif.

[73] Assignee: Pacesetter Systems, Inc., Sylmar, Calif.

[21] Appl. No.: 16,271

[22] Filed: Feb. 28, 1979

[51] Int. Cl.³ .................................................. A61N 1/36
[52] U.S. Cl. ............................................. 128/419 PG
[58] Field of Search ........ 128/419 P, 419 PG, 419 PS, 128/419 PT, 419 R, 421, 422, 690

[56] References Cited

U.S. PATENT DOCUMENTS

| | | | |
|---|---|---|---|
| 3,426,748 | 2/1969 | Bowers | 128/419 PT |
| 3,978,849 | 9/1976 | Geneen | 128/690 |
| 4,041,954 | 8/1977 | Ohara | 128/419 PT |
| 4,058,118 | 11/1977 | Stupay et al. | 128/690 |
| 4,164,944 | 8/1979 | Alley et al. | 128/419 PG |

FOREIGN PATENT DOCUMENTS

| | | | |
|---|---|---|---|
| 342356 | 3/1922 | Fed. Rep. of Germany | 128/419 R |
| 2826189 | 1/1979 | Fed. Rep. of Germany | 128/419 PG |

*Primary Examiner*—William E. Kamm
*Attorney, Agent, or Firm*—Freilich, Hornbaker, Wasserman, Rosen & Fernandez

[57] ABSTRACT

An apparatus and method for displaying and controlling parameters for a programmable living tissue stimulator system. Visual indicators corresponding to control parameters or signals for the tissue stimulator system are divided into a predetermined number of groups. One of these groups containing a parameter to be selected for the tissue stimulator system is selected, the selected group being identified by a visually identifiable indication. A parameter within that group is then selected for transmission to an implanted memory means which controls an implanted tissue stimulator. In a specific embodiment, a matrix of visual indicators consisting of R rows and S columns is provided, each visual indicator corresponding to a specific control signal. A means is provided whereby at least one visual indicator contained in a selected R row will blink on and off, the blinking indicators identifying control signals to be selected for the implanted memory means. Selection of a control signal within the selected R row causes the blinking to cease and the visual indicator corresponding to the selected signal to turn on when the selected signal is stored within the implanted memory means. Visual indicators corresponding to the unselected control signals in the selected R row turn off after a signal selection is made.

18 Claims, 9 Drawing Figures

DISPLAY AND CONTROL SYSTEM AND METHOD FOR PROGRAMMABLE LIVING TISSUE STIMULATOR

FIELD OF THE INVENTION

The invention relates to a display and control system for programmable living tissue stimulators such as heart pacemakers.

BACKGROUND OF THE INVENTION

Programmable living tissue stimulators such as programmable heart pacemakers or implantable drug pumps have been utilized in the medical field for several years. One example of a programmable tissue stimulator is disclosed in U.S. Pat. Application Ser. No. 957,410 filed on Nov. 3, 1978, now U.S. Pat. No. 4,197,850. A programmable tissue stimulator system typically comprises an implanted stimulating signal generator, an implanted memory means for storing control signals or parameters for the implanted signal generator, external programming means for generating control signals in accordance with predetermined input signals, means for transmitting control signals to the implanted memory means, and means for generating verification signals that indicate the transmitted control signals have been received by the implanted memory means. One shortcoming of programmable tissue stimulator systems, such as programmable pacemakers, is a capability to quickly and accurately select control signals to be stored in the implanted memory means by an apparatus that is readily transportable and can be easily utilized by an operator. Conventional methods for programming a programmable pacemaker typically consist of selecting a control signal to be stored in the implanted memory means through use of toggle switches or a plurality of control switches each corresponding to a control signal to be stored. Problems with such systems are that a switch corresponding to an incorrect control signal could be depressed, or a plurality of toggle switches could be incorrectly configured. There has long been a need for a control and display system for programmable pacemakers which minimizes the possibility of programming an incorrect control signal through operator error and provides visual feedback to an operator as to the control signals stored within the implanted memory means. The display and control system of the present invention provides such a system.

SUMMARY OF THE INVENTION

The invention provides a display and control system for a programmable living tissue stimulator system comprising a plurality of visual indicators divided into R groups of visual indicators. Each visual indicator corresponds to a control signal which could be stored in the implanted memory means. A means for selecting one of the R groups of visual indicators and a means for visually indicating that group of R indicators selected are provided. Another means is provided for selecting a control signal corresponding to one of the visual indicators in the selected R group of visual indicators. The means for selecting the R group of visual indicators and the means for selecting the indicator within the selected R group define the predetermined input signal which causes the external programming means to generate the control signal to be transmitted to the implanted memory means. The display and control system also provides a means for displaying control signals stored in the implanted memory means.

In a specific embodiment utilizing a programmable pacemaker, the plurality of visual indicators are located in a matrix having R rows and S columns, each visual indicator corresponding to a control signal which could be stored in the implanted memory means. The means for selecting one of the R rows of visual indicators comprises a plurality of switches, one switch being associated with each of the R rows. Selection of a specific R row results in at least one visual indicator within that row to blink on and off. The blinking indicators within the selected R row correspond to a control signal which can be selected for storage in the implanted memory means. In addition, a switch is provided for each of the S columns of the visual indicator matrix. Depression of the column switch containing one of the blinking indicators causes the control signal corresponding to that visual indicator to be transmitted to the implanted memory means and the blinking indicators to be turned off. Generation of a verification signal by the external programming means indicating that the control signal transmitted has been correctly received by the implanted memory means causes the visual indicator corresponding to the transmitted control signal to turn on. Thus, the invention provides a means whereby control signals which can be selected for storage within the implanted memory means are indicated by a first visually identifiable state, control signals not stored in the implanted memory means are indicated by a second visually identifiable state and control signals stored within the implanted memory means are indicated by a third visually identifiable state.

DETAILED DESCRIPTION

As required, a detailed illustrative embodiment of the invention is disclosed herein. This embodiment exemplifies the invention and is currently considered to be the best embodiment for such purposes. However, it is to be recognized that other means for implementing the logic functions described herein could be utilized. Accordingly, the specific embodiment disclosed is representative in providing a basis for the claims which define the scope of the present invention.

As previously explained, the invention provides a display and control system for a programmable living tissue stimulator system, such as a programmable heart pacemaker, in which a control signal to be stored within an implanted memory means can be readily selected, transmitted, and a verification signal displayed. In the specific embodiment to be described below, a plurality of visual indicators are located into a matrix having R rows and S columns, each visual indicator corresponding to a control signal for the implanted pacemaker.

Each R row has a corresponding selection switch, and each column has a corresponding selection switch. Upon pressing a selection switch for one of the R rows, at least one visual indicator within that row will begin blinking on and off. Selection of one of the S column switches corresponding to one of the visual indicators within the selected R row will then define to the pacemaker programmer a control signal to be stored within the implanted memory means. Upon confirmation that the correct control signal has been stored in the implanted memory means, a verification signal is supplied by the programmer to the display and control system. Pressing the S column selection switch also causes blinking of the visual indicators in the selected R row to stop, and the visual indicator corresponding to the selected control signal will turn on upon receipt of the verification signal, the other visual indicators being off. Thus, an operator can immediately visually verify that the control signal selected has been correctly transmitted and stored within the implanted memory means.

Figure 1:
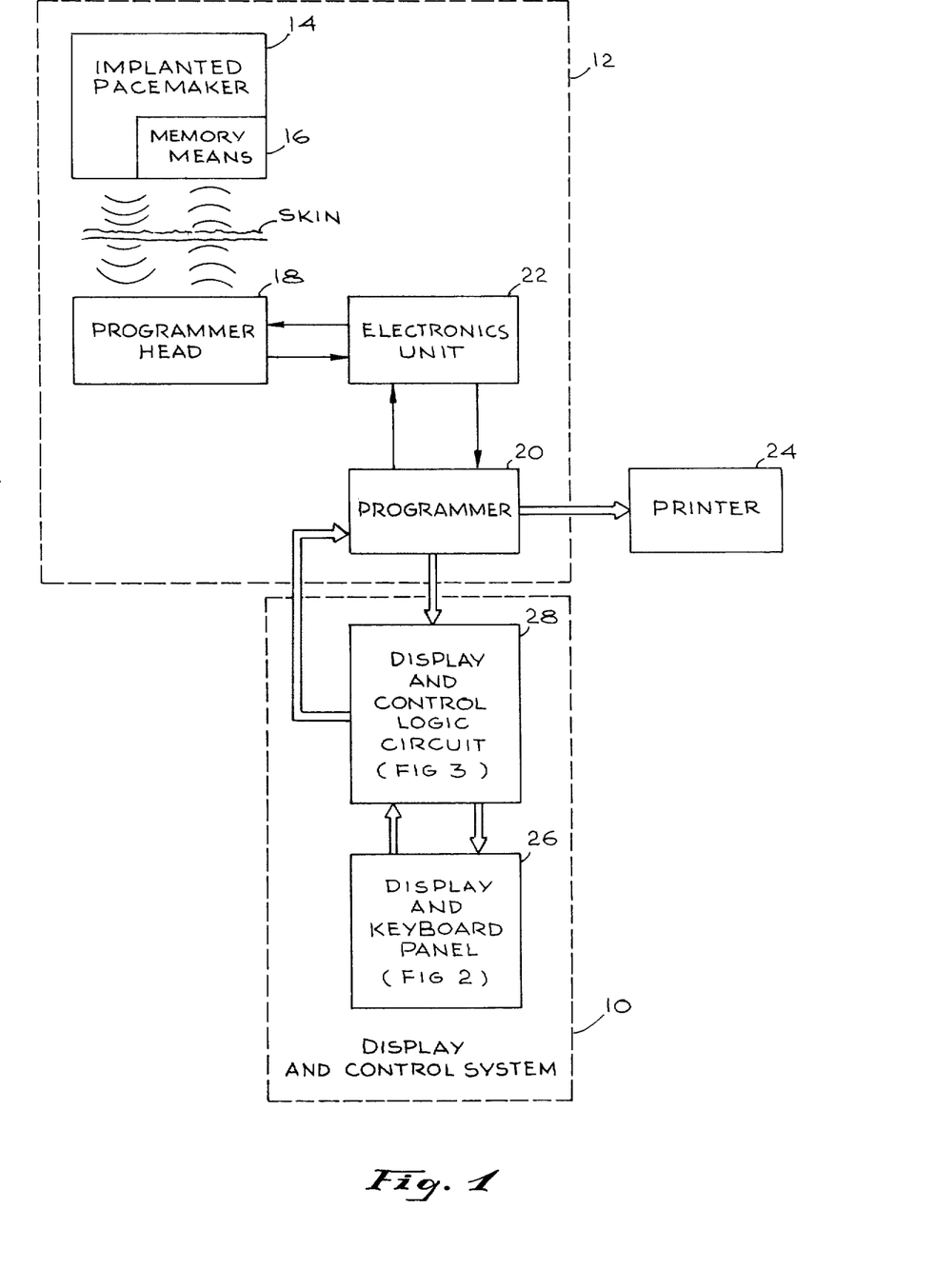
FIG. 1 is a block diagram of a programmable pacemaker system and the display and control system provided by the invention.

Referring to FIG. 1, a display and control system 10 provided by the invention is shown in conjunction with a programmable pacemaker system 12. Although a programmable pacemaker is used in this exemplary embodiment, a display and control system according to the invention could be used with any type of programmable living tissue stimulator. The programmable pacemaker system 12 comprises an implanted pacemaker 14 containing a programmable memory means 16. The implanted pacemaker 14 includes a tissue stimulator, power supply means, and associated electronics. The implanted pacemaker 14 and its associated memory means 16 can receive and store control parameters or signals transmitted by a programmer head 18, and transmit control signals stored within the memory means 16 to the programmer head 18. In addition, the implanted pacemaker 14 can transmit a plurality of control signals stored within its memory means 16 to the programmer head 18 upon receipt of an appropriate interrogate signal. Control signals to be transmitted to the implanted pacemaker 14 are generated within an externally located programmer 20 in accordance with certain predetermined input signals. The programmer 20 provides control signals to an electronics unit 22 and a printer 24. The electronics unit 22 provides an appropriately modulated signal to the programmer head 18. The programmer head 18 and implanted pacemaker 14 communication link is effected through magnetic coupling although electromagnetic coupling could also be utilized. A typical programmable pacemaker system is described in U.S. patent application Ser. No. 957,410, filed on Nov. 3, 1978.

The programmer 20 is configured to respond to predetermined input signals which address approrpiate programmer sections containing control signals corresponding to the predetermined input signals. Control signals are then generated by the programmer 20 for transmission via the electronics unit 22 to the implanted memory means 16. In addition, the programmer 20 provides a plurality of output verification signals to the display and control system 10, one of which corresponds to each control signal which could be stored in the implanted memory means 16. In this exemplary embodiment, a verification signal is in a logical "0" or low state when its corresponding control signal is stored in the implanted memory means 16 and a logical "1" or high state when it is not stored within the implanted memory means 16. Other features of the programmer 20 will be explained below. The display and control system 10 comprises a display and keyboard panel 26 and a display and control logic circuit 28. The display and control logic circuit 28 provides signals to and receives signals from the programmer 20 and the display and keyboard panel 26. As will be explained below, the display and control system 10 provides a means for effecting keyboard entries for controlling the programmer 20 which is particularly efficient and error-free by incorporation of a means to control various visual displays to be explained below in a unique and heretofor unutilized manner.

Figure 2:
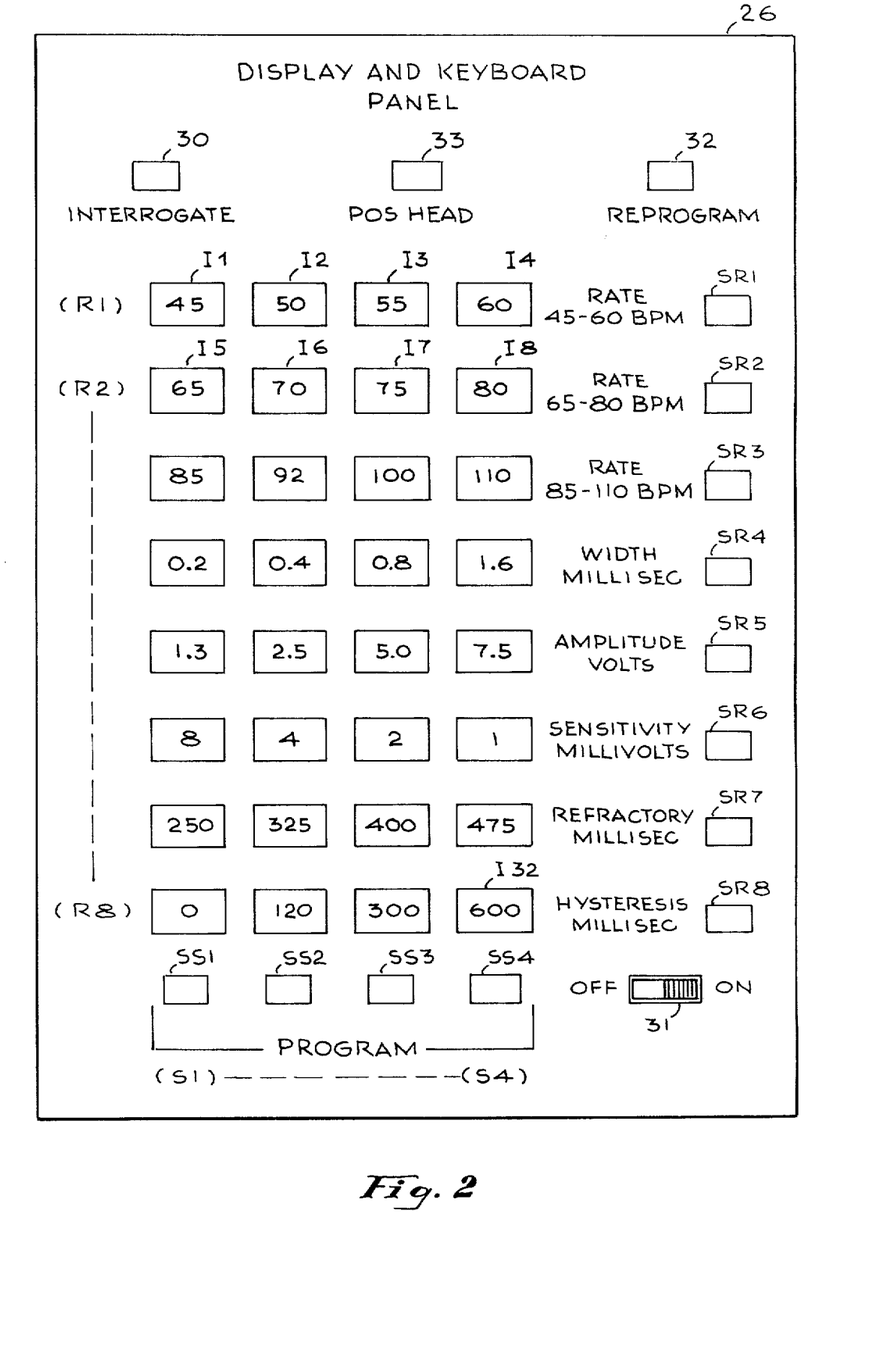
FIG. 2 shows the display and keyboard panel.

The display and keyboard panel 26 utilized in this exemplary embodiment is shown in FIG. 2. Referring to FIG. 2, a plurality of visual indicators I1 I32 are positioned so as to form eight rows R1 through R8 and aligned therein to form four columns S1 through S4. The first row of indicators is designated as row R1, the second row as R2, and the last row as R8. Similarly, the first column is designated as S1, the second column as S2, and the last column as S4. Any specific indicator can be designated by referring to its corresponding R row and S column. Thus, a rate of 70 beats per minute can be designated by referring to row R2 and column S2. The indicator lights I1 through I32 in the exemplary embodiment comprise LCD's each having a specific number corresponding to a control signal which could be stored in the implanted memory means 16. In the particular display shown, the first row R1 corresponds to heart rates between 45 and 60 beats per minute, the first visual indicator I1 referring to 45 beats per minute and the fourth visual indicator I4 referring to 60 beats per minute. As can be seen, the second row R2 refers to rates between 65 and 80 beats per minute and the third row R3 to rates between 85 and 110 beats per minute. Other characteristics of a heart stimulation pulse such as width, amplitude, sensitivity, refractory and hysteresis are provided. Each of the visual indicators I1 through I32 corresponds to the specific value of a control signal that can be stored within the implanted memory means 16. Thus, a control signal corresponding to visual indicator I5 would cause heart stimulation pulses to be generated at a rate of 65 beats per minute by the implanted pacemaker 14. A first plurality of switches SR1 through SR8 are provided, one switch corresponding to each of the eight R rows. A second plurality of switches SS1 through SS4 are also provided, one switch corresponding to each of the four S columns. Additional switches include an interrogate switch 30 and a power on switch 31. A reprogram visual indicator 32 and a position head indicator 33 are also provided. Utilizing amplitude of the stimulation pulse as an example, an operator has a choice of selecting four amplitudes of 1.3, 2.5, 5.0 or 7.5 volts as can be seen in row R5.

Although the eight R rows have been shown in a horizontal orientation with respect to the bottom of the display and keyboard panel 28 and the four S columns in a vertical orientation, the R rows and S columns are not defined with respect to any particular orientation. Thus, the rows could be oriented vertically with respect to the bottom of the display and keyboard panel 28, or at any other desired angle.

In operation, the display and keyboard panel 28 is used as follows. At initial power turn-on, all of the visual indicators I1 through I32, 32 and 33, are activated for approximately two seconds, thereby indicating to an operator that all are in working order. An operator then presses the interrogate switch 30 which in turn causes the programmer 20 to generate an interrogate signal which is transmitted to the implanted pacemaker 14. The transmitted interrogate signal causes the implanted pacemaker 14 to telemeter to the programmer head 18 the control signals stored in the implanted memory means 16. These control signals are recognized by the programmer 20 and verification signals are provided to the display and control system 10 so that each stored control signal is displayed on its corresponding visual indicator. Thus, one of the visual indicators I1 through I12 in the first three rows R1 through R3 will be activated indicating the beats per minute rate of the implanted pacemaker 14. Likewise, the control signals defining pulse width, amplitude, sensitivity, refractory and hysteresis will also be displayed, one visual indicator being on in each of their respective rows. If an operator desires to change a control signal, he would press one of the row switches SR1 through SR8 corresponding to a row containing the desired control signal. For example, if the display indicates that the memory means 16 contains a control signal corresponding to 55 beats per minute, and if the operator wants to change the rate to 75 beats per minute, he would depress switch SR2 corresponding to row R2. Depressing switch SR2 will cause all visual indicators I5 through I8 in row R2 to blink on and off at a rate of approximately 1.5 blinks per second, the blinking lights indicating to the operator those control signals which can be selected for storage within the implanted memory means. Since the rate to be selected is 75 beats per minute, the operator then depresses the column switch SS3 which is directly below the visual indicator showing 75 beats per second. Depression of switch SS3 will cause the visual indicators in row R2 to stop blinking, and upon confirmation that the selected control signal of 75 beats per minute is stored within the memory means 16, the visual indicator I7 will turn on the and visual indicator I3 in the first row R1 will turn off. This will indicate to the operator that the memory means 16 is now programmed with a control signal corresponding to 75 beats per minute. If the operator desired to increase the rate from 55 beats per minute to 60 beats per minute, the 55 beat per minute visual indicator I3 being on, depression of the first row switch SR1 will only cause the remaining indicators I1, I2, and I4 in that row to blink. Selection of the appropriate column switch SS4 will then cause the control signal corresponding to 60 beats per minute to be transmitted to the implanted memory means 16.

In the event that one of the column switches SS1 through SS4 is depressed, and a signal is not received by the programmer 20 that the selected signal is stored in the implanted memory means 16, the programmer 20 generates a reprogram signal which causes the reprogram indicator 32 to turn on. The visual indicator I3 corresponding to the previously stored control signal is blanked by the programmer 20. In addition, if the programmer head 18 is incorrectly positioned with respect to the implanted pacemaker 14, a position head signal is generated which lights the position head indicator 33.

The display and control logic circuit 28 provides a means whereby the above-described displays and keyboard or switch entries can be utilized by an operator to visually select control signals for storage in the implanted memory means 16, the specific visual indications providing a means which will tend to reduce errors and make selection as positive as possible. Also, as one can appreciate, any number of rows of control signals can be provided, and any number of columns can be provided in accordance with the maximum number of visual indicators in any specific row. It is not necessary that each row have a visual indicator corresponding to each column; for example, row R3 could provide only three rate selections 85, 92 or 100. However, it is important that the selections provided are within one of the designated columns in order to facilitate identification of the control signal to be selected.

Figure 3A:
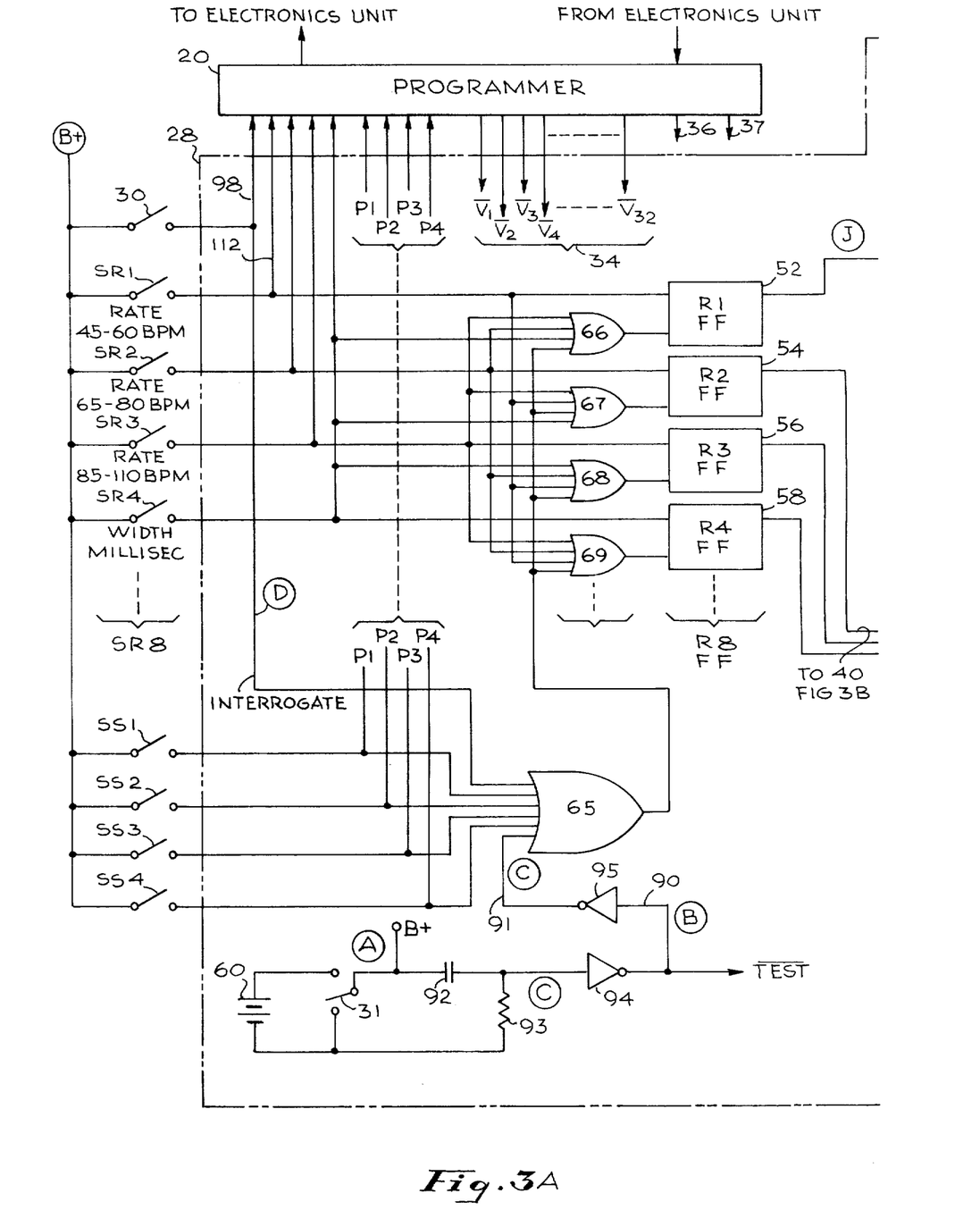
FIGS 3A–3C are a diagram of the display and control logic circuit and its interface with the pacemaker programmer.
Figure 3B:
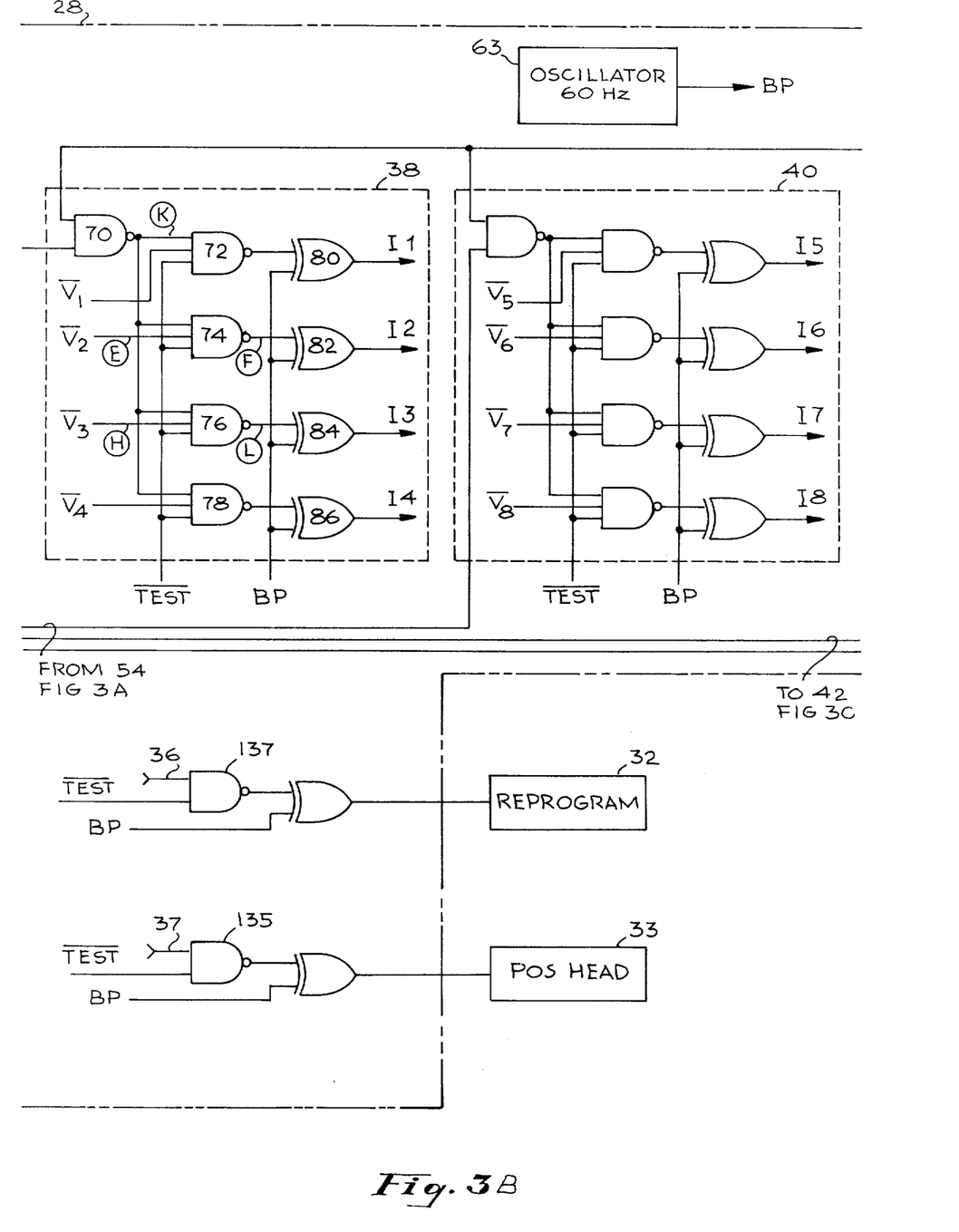
Figure 3C:
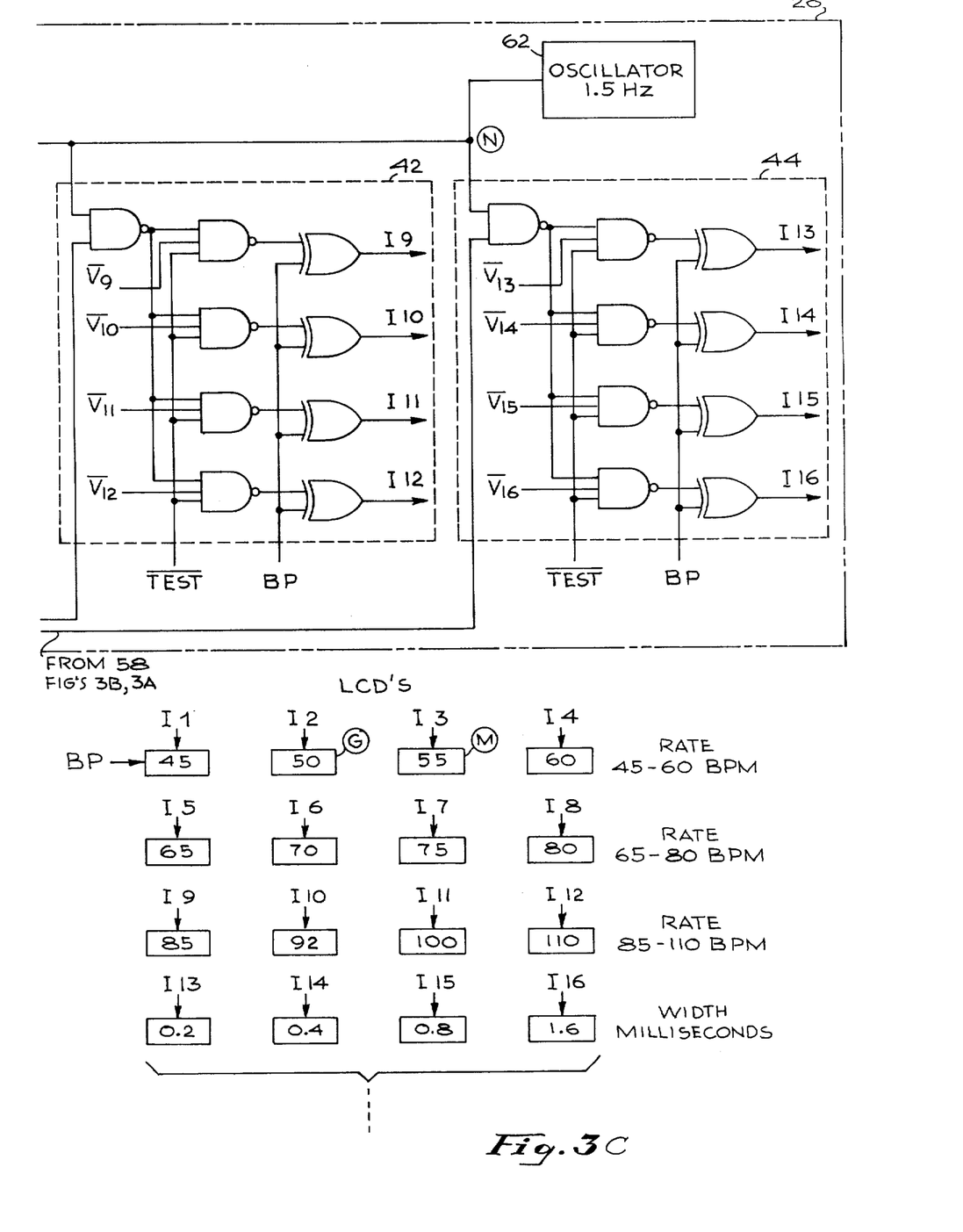

Referring now to FIG. 3, the display and control logic circuit 28 has inputs comprising lines corresponding to each of the switches SR1 through SR8, SS1 through SS4, and the interrogate switch 30 on the display and keyboard panel 28. These same input lines are supplied through the display and control logic circuit 28 to the programmer 20. A high signal on one of the row switches combined with a high signal on one of the column switches defines a specific control signal. The programmer 20 is configured so that a location containing the defined control signal is addressed by the two high signals. The information contained in the addressed location provides an appropriate signal for transmission to the implanted pacemaker 16. The programmer 20 also provides 32 output signals on signal verification lines $\overline{V}1$-$\overline{V}32$ shown at 34 which digitally indicate those control signals stored in the implanted memory means 16. One signal verification line corresponds to each of the visual indicators I1 through I32. The programmer 20 also provides a reprogram signal on a reprogram line 36 which indicates that a transmitted control signal was not stored in the memory means 16 and a position head signal on a position head line 37 which indicates that the programmer head 18 is improperly positioned with respect to the implanted pacemaker 14.

Logic circuitry for each of the visual indicators within a specific row is shown within separate blocks. Thus, logic circuitry within dotted lines 38 provides signals to drive visual indicators I1 through I4, and logic circuitry within dotted lines 40, 42 and 44 drives visual indicators I5 through I8, I9 through I12, and I13 through I16 respectively. Although only four blocks are shown, there are equivalent logic circuitry blocks, row selection switches, and visual indicators not shown for each of the R rows. Also provided are row flip-flops 52, 54, 56 and 58 corresponding to each of the row switches SR1, SR2, SR3 and SR4 respectively. Not shown are the row flip-flops corresponding to switches SR5 through SR8. A power supply which in the exemplary embodiment is a battery 60 is provided. A square wave oscillator 62 having an output signal of approximately 1.5 cycles per second is provided, this signal causing various visual indicators to blink as will be explained below. In addition, reset OR gates 65, 66, 67, 68 and 69 provide a reset pulse for the row flip-flops 52, 54, 56 and 58 each time one of the column switches SS1 through SS4, a different row switch, or the interrogate switch 30 is depressed, or power is turned on. As is well known to those familiar with LCD displays, their life is greatly extended when they are subjected to an alternating current during periods of operation. Each of the LCD's I1-I32 has an associated backplane. A 60 Hz voltage signal is applied to each LCD backplane by a backplane oscillator 63, as shown for indicator I1 in FIG. 3. Not shown are backplane signals for each of the other LCD's.

Logic circuits 38, 40, 42 and 44 associated with each visual indicator group I1 through I4, I5 through I8, I9 through I12, etc., are identical as previously explained.

Referring to the logic circuit 38 associated with visual indicators I1 through I4, an oscillator-controlling NAND gate 70 is connected to the R1 flip flop 52 and to the square wave oscillator 62. The output of the oscillator controlling NAND gate 70 is provided to four input NAND gates 72, 74, 76 and 78. Each input NAND gate also has as an input one of the signal verification lines 32 from the programmer 20 which corresponds to its associated visual indicator. Thus input NAND gate 72 has signal verification line $\overline{V1}$ as one input, NAND gate 74 has signal verification line $\overline{V2}$ as one input, etc. Also, each input NAND gate has $\overline{TEST}$ as an input, the generation of $\overline{TEST}$ to be explained below. Each input NAND gate 70, 72, 74 and 76 has an associated output Exclusive-OR gate 80, 82, 84 and 86 respectively, the outputs of which drive the visual indicators I1-I4. The Exclusive-OR gates also have the output of the backplane oscillator 63 as an input, this signal being provided so as to generate the alternating current for each operating LCD as previously explained. As will be explained below, when the output of the Exclusive-OR gate is in phase with the backplane oscillator 63, its associated LCD will be off, when it is out of phase with the backplane oscillator its associated LCD will be on.

Figure 4:
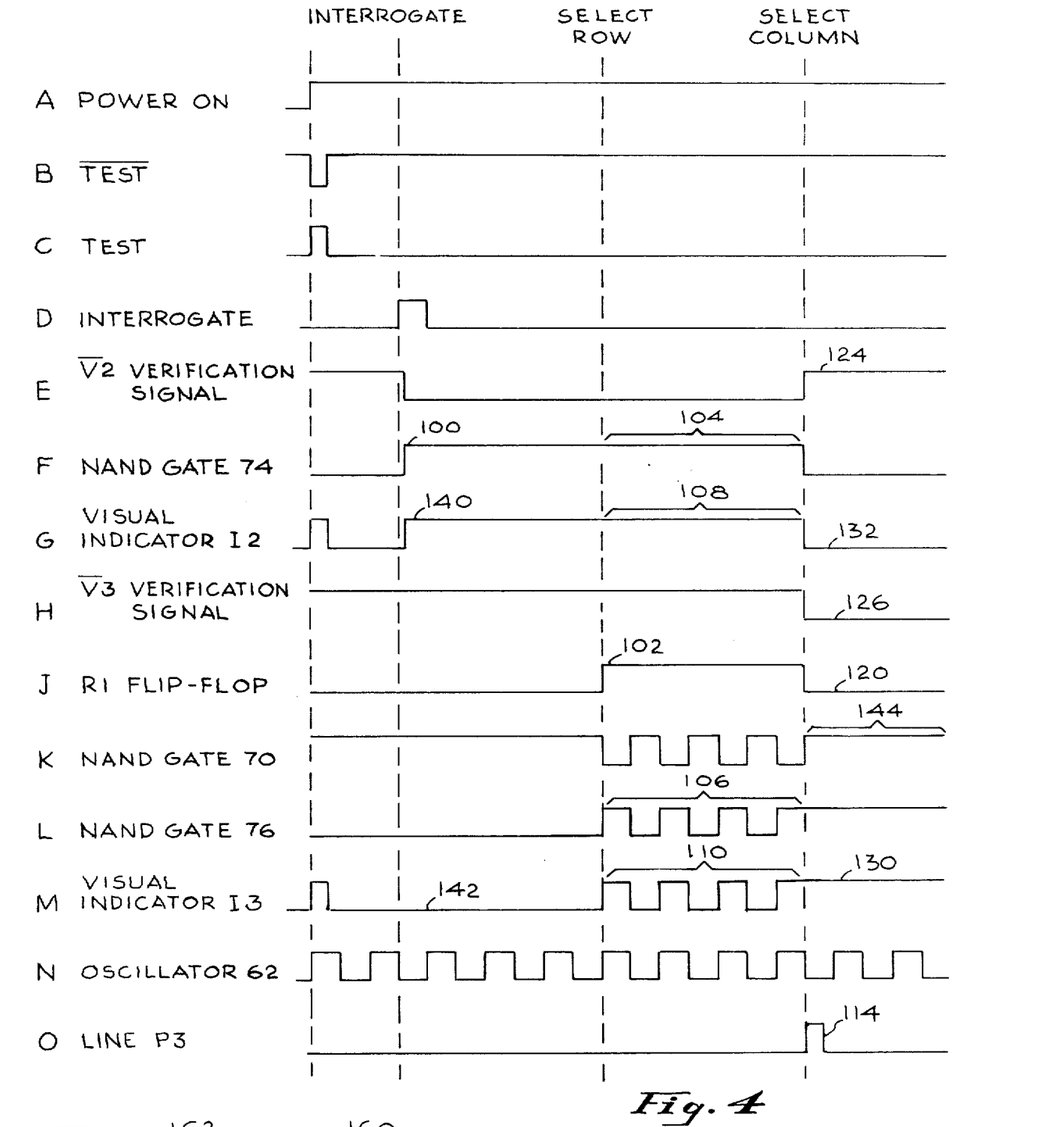
FIG. 4 shows various waveforms within the display and control logic circuit of FIG. 3.

Operation of the display and control logic circuit 28 shown in FIG. 3 can best be understood in conjunction with the various waveforms shown in FIG. 4. Referring to FIG. 4, waveform A reflects the state of the power-on switch 31. Turning power on provides a $\overline{TEST}$ signal on line 90 and a TEST signal on line 91 as shown in waveforms B and C respectively. The TEST signal on line 91 creates a pulse at the output of OR gate 65, which in turn resets the row flip-flops 52, 54, 56 and 58 through the reset OR gates 66, 67, 68 and 69. The TEST and $\overline{TEST}$ signals are generated by a capacitor 92 in conjunction with a pull down resistor 93, their values being chosen so as to provide a pulse of approximately 2 seconds duration. A first inverting amplifier 94 creates the $\overline{TEST}$ signal from the TEST signal, and a second inverting amplifier 95 recreates the TEST signal from the $\overline{TEST}$ signal. When the $\overline{TEST}$ signal is present, the outputs from the input AND gates 72, 74, 76 and 78 will be high, thereby resulting in the outputs from the Exclusive-OR gates 80, 82, 84 and 86 to have a frequency equal to that of and out of phase with the backplane oscillator 63. This alternating current causes the visual indicators I1-I4 to remain on until the $\overline{TEST}$ pulse terminates. At this time, the outputs of the Exclusive-OR gates are in phase with the signal from the backplane oscillator 63, thereby resulting in no illumination of the visual indicators. Thus, the two second duration of the $\overline{TEST}$ pulse provides a two-second period at initial power turn-on during which all visual indicators will light, thereby providing an operator a means for determining that all visual indicators are functioning properly. By way of further explanation, a high input to one of the Exclusive-OR gates 80, 82, 84 or 86 results in an output signal 180 degrees out of phase with the output of the backplane oscillator 63. These two signals when supplied across an LCD causes it to be continuously illuminated by an alternating current for the reasons previously explained. Likewise, a low input to the Exclusive-OR gates result in an output that is in phase with the backplane oscillator 63, thereby resulting in no voltage differential across or current through the LCD.

Depression of the interrogate switch 30 provides a signal shown in waveform D to the programmer 20 through an interrogate line 98 and resets the row flip-flops 52, 54, 56 and 58 through the OR gate 65. As a result of the signal provided on the interrogate line 98 to the programmer 20, the control signals stored within the implanted memory means 16 are provided to the programmer 20 as previously explained. Each of the signal verification lines 34 corresponding to a stored control signal contains a low signal, the other verification lines containing a high signal. Assume for exemplary purposes that a control signal stored in the memory means 16 corresponds to 50 beats per minute which in turn corresponds to visual indicator I2. As a result of the interrogation, the programmer 20 provides a low output on verification line $\overline{V2}$ as shown in waveform E which corresponds to 50 beats per minute. Thus, outputs on verification lines $\overline{V1}$, $\overline{V3}$ and $\overline{V4}$ will be high indicating that control signals corresponding to 45, 55, and 60 beats per minute are not stored within the implanted memory means 16. As a result of verification signal $\overline{V2}$ being low, the output of the input NAND gate 74 as shown in waveform F at 100 will be high, thereby causing the output of the Exclusive-OR gate 82 driving visual indicator I2 to be out of phase with the output of the backplane oscillator 63 as previously explained. Thus, the verification signal $\overline{V2}$ being low causes indicator I2 to illuminate and indicate that a control signal corresponding to 50 beats per minute is stored in the implanted memory means 16. Waveform G represents the state of visual indicator I2, a high state corresponding to an "ON" condition and a low state corresponding to an "OFF" condition.

As previously indicated, verification signal $\overline{V3}$ remains high as a result of the interrogation, this signal being shown in waveform H. Since the R1 flip-flop 52 was reset as a result of initial power turn-on as shown in wave form J, the output of the oscillator-controlling NAND gate 70 will be high as shown in waveform K. The other input $\overline{TEST}$ to NAND gate 76 is also high, thereby resulting in a low output as shown in waveform L and no illumination of visual indicator I3 as shown in waveform M. The same analysis applies to the visual indicators I1 and I4. Thus, as long as the R1 flip-flop 52 is in a reset or low configuration, the status of the visual indicators I1-I4 is controlled by their respective signal verification lines $\overline{V1}$-$\overline{V4}$.

The square wave oscillator 62 provides a square wave output signal shown in waveform N. This square wave output is provided as one input to the oscillator-controlling NAND gate 70. As previously explained, a row selection switch SR1 through SR8 must be depressed in order to identify an R group of control signals from which one is to be selected. In the example being described, SR1 is depressed, thereby causing its associated R1 flip-flop 52 to be set. The resulting high output from the R1 flip-flop 52 is provided as one input to the oscillator-controlling NAND gate 70. This signal corresponds to that shown in waveform J of FIG. 4 and occurs at the time indicated by 102. This high input to the oscillator-controlling NAND gate 70 causes a square wave output to be formed as shown in waveform K, the output being inverted with respect to the square wave oscillator 62 output. This square wave output is then provided to each of the input NAND gates 72, 74, 76 and 78, the output of NAND gate 74 shown in waveform F at 104 remains high because verification signal $\overline{V2}$ shown in waveform E is low. However, NAND gate 76 has a square wave output during the interval shown at 106, because its other input signals $\overline{TEST}$ and $\overline{V3}$ are high. By a similar analysis, it can be shown that the other input NAND gates 72 and 78 also have square outputs created as a result of the R1 flip-flop 52 being set. Thus, the visual indicator I2 remains on as shown by 108 in waveform G whereas visual indicator I3 blinks at a rate of 1.5 Hz as shown by 110 in waveform M. Visual indicators I1 and I4 also blink as explained above. Thus, upon depression of the rate switch SR1, three of the visual indicators I1, I3 and I4 will begin to blink while visual indicator I2 corresponding to the control signal stored in the memory means 16 will remain on.

In this illustrative example, it is desired to store the control signal associated with visual indicator I3 in the implanted memory means 16. Referring to FIG. 2, it can be seen that selection of that control signal will require depression of column switch SS3. Referring again to FIG. 3, depression of switch SS3 will provide a signal on line P3 which is provided as an input to the programmer 20. Thus, the programmer 20 has received input signals occurring on an input line 112 corresponding to switch SR1 and on line P3 corresponding to switch SS3. The signal appearing on line P3 is shown in waveform O of FIG. 4 at 114. The two signals appearing on line 112 and on line P3 are used by the programmer 20 to address a memory section defining the control signal associated with visual indicator I3. As previously explained, this control signal is transmitted to the implanted memory means 16 and a verification signal provided by the programmer 20 on line $\overline{V3}$. This results in the signal on verification line $\overline{V2}$ to revert to a high condition and the signal appearing on verification line $\overline{V3}$ to become low. Referring again to FIG. 4, when the programmer switch SS3 is depressed and the pulse shown at 114 appears on its output line P3, the R1 flip-flop 52 associated with rate switch SR1 is reset as shown at 120 by a corresponding pulse appearing at the output of the reset OR gates 65 and 66. This resetting of the R1 flip-flop 52 blocks the square wave oscillator 62 output from reaching any of the input NAND gates 72, 74, 76 or 78. As a result of changing the control signals stored in the implanted memory means 16, the signal on line $\overline{V2}$ becomes high as shown at 124 and the signal on line $\overline{V3}$ becomes low as shown at 126. This reversal causes visual indicator I3 to be "ON" as shown in waveform M at 130 and visual indicator I2 to be "OFF" as shown in waveform G at 132. In the event that the programmer head 18 is incorrectly positioned with respect to the implanted pacemaker 14, a position head signal on line 37 goes low. This low signal causes the output of a position head NAND gate 135 to go high, thereby illuminating the position head indicator 33. In a similar manner, if a verification signal is not received as a result of transmitting a control signal, a reprogram signal on line 36 goes low, thereby causing the output of a reprogram NAND gate 137 to go high and illuminate the reprogram indicator 32.

To summarize operation of the display and control logic curcuit 28, referring again to FIG. 4 one can see that turning on the power as shown in waveform A, a $\overline{\text{TEST}}$ signal is generated which causes all visual indicators to illuminate as shown in waveforms G and M. Depression of the interrogate switch 30 as shown in waveform D causes signal verification signals as shown in waveform E, to become low when their corresponding control signals are stored in the implanted memory means 16. The visual indicator I2 associated with a control signal present in the implanted memory means 16 is turned on as shown at 140 when its corresponding signal verification signal $\overline{V2}$ goes low. The visual indicator I3 associated with a control signal not stored in the implanted memory means 16 is off as illustrated in waveform M at 142. Upon depression of switch SR1 as shown in waveform J at 102, a square wave drive signal is provided to the visual indicators not corresponding to stored control signals as shown in waveform M at 110. Upon depression of the column switch SS3 as shown in waveform O at 114, the square wave driving signal is blocked as shown in waveform K at 144 and the visual indicator I3 corresponding to the selected control signal comes on as shown in waveform M at 130 and the visual indicator I2 associated with a changed control signal is turned off as shown in waveform G at 132.

Figures 5A, 5C:
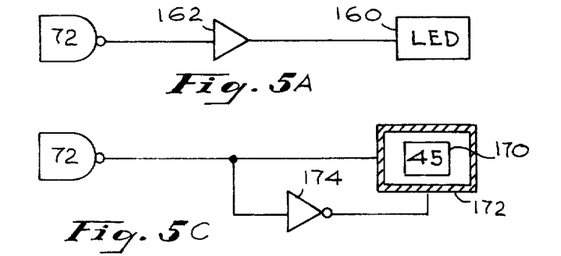
FIGS. 5A, 5B, and 5C show various types of visual indicators which could be used in the display and keyboard panel.
Figure 5B:
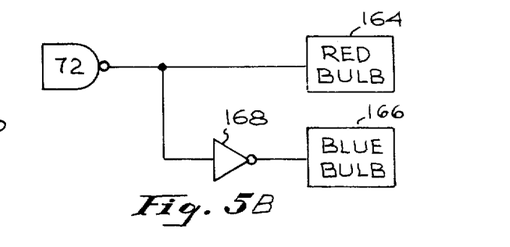

Although in the exemplary embodiment, LCD's have been chosen for the visual indicators, other types of visual indicators could also be utilized. For example, referring to FIG. 5A, a light emitting diode (LED) 160 could be connected to the output of an input NAND gate 72 through a buffer 162 and utilized as a visual indicator in lieu of an LCD. An incandescent bulb could also be utilized. Colored displays could be utilized as shown in FIG. 5B. The output from the input NAND gate 72 drives a red bulb 164 when in a high state and a blue bulb 166 through an inverting amplifier 168 when in a low state. This provides a color-coded indicator to indicate a selected control signal and an unselected control signal. Another type of indicator shown in FIG. 5C comprises a geometrically discriminating display in which a number 170 is illuminated when the output from the input NAND GATE is high and a square 172 is illuminated by an inverting amplifier 174 when the output is low.

The above-described embodiment utilizes discrete logic elements to implement the teachings of the invention. However, it will be recognized by those familar with digital circuits that other means could be utilized to implement the logic functions described above. For example, a read only memory (ROM) could be programmed to provide outputs to the display and keyboard panel 26 identical to those described above. Thus it should be recognized that any means implementing the logic functions described above are covered by the claims which define the scope of the present invention.

Thus, it should be apparent that a display and control system for a programmable living tissue stimulator system has been disclosed which provides a means for presenting a visual display in which groups of control signals can be selected and then an individual control signal within the selected groups selected for transmission to an implanted memory means, and a means for presenting visually identifiable indications for selected control signals, unselected control signals, and control signals to be selected.

What is claimed is:

1. In combination with a programmable living tissue stimulator system having an implanted stimulating signal generator, an implanted programmable memory means for storing control signals for said implanted signal generator, external programming means for generating control signals in accordance with predetermined input signals, means for transmitting control signals to said implanted memory menas, means for generating verification signals that indicate said transmitted control signals have been received by said implanted memory means, a display and control system comprising:

a plurality of visual indicators each corresponding to a control signal, said visual indicators being divided into R groups of visual indicators;

first means for selecting one of said R groups of visual indicators;

means for causing a first visually identifiable indication to be provided by said selected R group of visual indicators;

second means for selecting a control signal corresponding to one of said visual indicators in said selected R group of visual indicators, said first and second means for selecting defining said predetermined input signals to said external programming means for generating said selected control signal;

means for causing a second visually identifiable indication to be provided by said visual indicators corresponding to unselected control signals in said selected R group of visual indicators; and means for causing a third visually identifiable indication to be provided by said visual indicator corresponding to said selected control signal when a verification signal corresponding to said selected control signal is generated.

2. The display and control system of claim 1 in which said first means for selecting comprises a first plurality of switches each corresponding to one of said R groups of visual indicators and said second means for selecting comprises a second plurality of switches each corresponding to an order of a visual indicator within an R group of visual indicators.

3. The display and control system of claim 2 in which said means for causing a first visually identifiable indication comprises means for causing said at least one visual indicator to blink on and off, said means for causing a second visually identifiable indication comprises means for causing said visual indicators corresponding to unselected control signals to be off, and said means for causing a third visually identifiable indication comprises means for causing said visual indicator corresponding to said selected control signal to be on.

4. The display and control system of claim 1 in which said visual indicators comprise LCD's.

5. The display and control system of claim 1 in which said visual indicators comprise light emitting diodes (LED's).

6. The display and control system of claim 1 in which said visual indicators comprise color-coded indicators having one color in the presence of an excitation signal and another color in the absence of an excitation signal.

7. The display and control system of claim 1 in which said external programming means comprises means for determining control signals stored in said implanted memory means in response to an interrogate signal and means for providing verification signals corresponding to said stored control signals, said display and control system further comprising:

switch means for providing said interrogate signal to said external programming means; and means responsive to said verification signals for causing visual indicators corresponding to control signals stored in said memory means to provide said third visually identifiable indication.

8. The display and control system of claim 1 in which said external programming means comprises means for generating a reprogram signal when a verification signal corresponding to said selected control signal is not generated, said display and control system further comprising visual display means for indicating presence of said reprogram signal.

9. The display and control system of claim 1 in which said external programming means comprises means for generating a position head signal when said transmitting means is not within a predetermined distance from said implanted stimulating signal generator, said display and control system further comprising visual display means for indicating presence of said position head signal.

10. A display and control system for a programmable living tissue stimulator system comprising:

a plurality of visual indicators located in a matrix having R rows and S columns, each visual indicator corresponding to a control signal for said tissue stimulator system;

first means for selecting one of said R rows of visual indicators;

means for visually indicating said selected R row;

second means for selecting one of said S columns;

means for providing an output to said tissue stimulator system corresponding to a control signal defined by said selected R row and said selected S column; and means for displaying a verification signal from said tissue stimulator system corresponding to said control parameter defined by said selected R row and said selected S column.

11. The display and control system of claim 10 in in which said first means for selecting comprises a plurality of row selection switches each corresponding to one of said R rows and said second means for selecting comprises a plurality of column selection switches each corresponding to one of said S columns.

12. The display and control system of claim 10 in which said means for visually indicating said selected R row comprises means for causing said visual indicators comprising said selected R row to provide a first visually identifiable indication.

13. The display and control system of claim 12 further comprising means for causing said visual indicators in said selected R row but not in said selected S column to provide a second visually identifiable indication.

14. The display and control system of claim 13 in which said means for displaying a verification signal from said stimulator system comprises means for causing said visual indicator corresponding to said verification signal control signal to provide a third visually identifiable indication.

15. The display and control system of claim 14 in which said visual indicators are LCD's, and said first visually identifiable indication is an alternating "on-off" indication, said second visually identifiable indication is an "off" indication, and said third visually identifiable indication is an "on" indication.

16. The display and control system of claim 10 further comprising:

means for providing an interrogate signal to said tissue stimulation system; and means for causing said visual indicators to provide visually identifiable indications responsive to verification signals provided by said tissue stimulator system as a result of said interrogate signal.

17. The display and control system of claim 10 further comprising means for displaying a position head signal provided by said stimulator system.

18. A method for displaying and controlling parameters for a programmable living tissue stimulation system, the steps comprising:

locating a plurality of visual indicators in a matrix having R rows and S columns, each visual indicator corresponding to a control signal for said stimulator system;
selecting one of said R rows;
visually indicating said selected R row;
selecting on of said S columns;
providing an output to said tissue stimulator system corresponding to a control signal defined by said selected R row and said selected S column; and
displaying a verification signal from said tissue stimulator system corresponding to said control signal defined by said selected R row and said selected S column.

* * * * *